United States Patent [19]

Blake-Coleman et al.

[11] Patent Number: 4,848,139
[45] Date of Patent: Jul. 18, 1989

[54] DETERMINING AMOUNT OF BIOLOGICAL MATERIAL

[75] Inventors: Barry C. Blake-Coleman; David J. Clarke, both of Wiltshire, United Kingdom

[73] Assignee: Public Health Laboratory Service Board, United Kingdom

[21] Appl. No.: 148,164

[22] Filed: Feb. 1, 1988

Related U.S. Application Data

[63] Continuation of Ser. No. 829,645, Jan. 31, 1986, abandoned.

[30] Foreign Application Priority Data

Apr. 3, 1984 [GB] United Kingdom ................. 8408527
Apr. 3, 1984 [GB] United Kingdom ................. 8408528

[51] Int. Cl.$^4$ ........................ G01N 33/487; G01N 9/00
[52] U.S. Cl. .................................... 73/61 R; 73/32 A; 435/39; 435/291
[58] Field of Search ............... 73/32 A, 61 R; 435/29, 435/39, 291

[56] References Cited

U.S. PATENT DOCUMENTS

| | | | |
|---|---|---|---|
| 3,555,880 | 1/1971 | Menius et al. | 73/32 A |
| 4,074,562 | 2/1978 | North | 73/32 A |
| 4,217,774 | 8/1980 | Agar | 73/32 A |
| 4,242,096 | 12/1980 | Oliveira et al. | 310/312 |
| 4,246,344 | 1/1981 | Silver | 73/61 R |
| 4,566,312 | 1/1986 | Collins et al. | 73/32 A |

FOREIGN PATENT DOCUMENTS 229430 11/1985 German Democratic Rep. ... 435/39

OTHER PUBLICATIONS

A. Shons et al., "An Immunospecific Microbalance," *J. Biomed. Mater. Res.*, No. 6 (1972), pp. 565-570.
Leopold et al., "The Application of the Mechanical Oscillator Technique for the Determination of the Density of Physiological Fluids," *Biomedical Techniques*, 22 (1977), pp. 231-234.
Balls, "A New On-Line Density Meter for Viscous Liquids and Slurries," *Advances in Instrumentation*, 35 (1980), pp. 1-13.

Primary Examiner—John Chapman
Attorney, Agent, or Firm—Lowe, Price, LeBlanc, Becker & Shur

[57] ABSTRACT

Apparatus for determining the amount of biological material in a fluid medium, typically the concentration of bacteria in a fermentation chamber, has a test cell through which a medium can be passed with bacteria or after bacteria have been removed by filtration. In the test cell a vibratory element is excited to a resonant frequency indicative of density and a comparison of medium density and medium plus bacteria density reveals the bacteria concentration.

14 Claims, 8 Drawing Sheets

DETERMINING AMOUNT OF BIOLOGICAL MATERIAL

This application is a continuation of Application Ser. No. 829,645, filed Jan. 31, 1986, abandoned.

This invention relates to methods and apparatus for determining the amount of biological material in a system and, in one important example, to methods and apparatus for determining the number of microorganisms contained in a fluid medium.

In a wide variety of laboratory and industrial scale fermentation processes, it is important to know the numbers of or concentrations of microorganisms - typically bacteria - in given systems.

Bacteria can be counted directly with optical microscopy using a measurement cell of known volume. The procedure is, however, tedious and time-consuming. It has become common to use the optical transmission of a sample, at a predetermined wavelength, as a measure of the number of bacteria contained in suspension. Optical density measurements are complicated, however and usually involve spectrophotometers and sample processing. For this and other reasons, they are not easily adapted to on-line measurements. A further difficulty is that if a wide range of measurements is to be achieved, the necessary levels of dilution reduce accuracy.

It is an object of the present invention to provide an improved method and apparatus for measuring the amount of biological material suspended in a fluid medium, which is accurate over a wide concentration range and which is suited to on-line use.

Accordingly, the present invention consists, in one aspect, in a method of determining the amount of biological material contained in a fluid medium, comprising the steps of exciting a vibratory element in contact with the medium, monitoring said vibratory motion to obtain a value for the density and deriving from said density value a measure of the amount of biological material.

Sometimes, there will be a single-valued relationship between, say, the concentration of bacteria in a nutrient medium and the composite density of the medium plus bacteria. More usually, however, it will be necessary to make two separate density measurements. In a preferred form of the invention, therefore, the steps of exciting and monitoring the motion of a vibratory element are repeated after removal of said biological material so as to obtain a value for the density of the medium and wherein said measure of the amount of biological material is derived from a comparison of density values for the suspension and for the medium.

In another aspect, the present invention consists in a method of measuring the concentration of biological particles in a flowing medium, using at least one test cell having a vibratory element the motion of which is monitored to provide a measure of the density of the flow in the test cell, comprising the steps of directing the flow of medium containing the biological particles through the test cell; obtaining a first measure of density; separating biological particles from the medium; directing the separated medium through the test cell or one of the test cells; obtaining a second measure of density and deriving from comparison of said first and second measures of density a value for the concentration of biological particles in the medium.

Suitably, one test cell is used and the step of directing medium from which biological particles have been removed through the test cell comprises diverting the flow along the path containing a filter adapted to remove the biological particles.

Alternatively, two test cells are used and the step of directing medium from which biological particles have been removed through one of the test cells comprises splitting the flowing medium into two flow paths each containing a test cell, one flow path including a filter upstream of the associated test cell.

Advantageously, the vibratory element is brought to resonance through feedback and the resonant frequency measured to indicate density.

It is a further object of this invention to provide improved apparatus for measuring the concentration of biological particles in a flow of medium.

Accordingly, in a further aspect, the present invention consists in apparatus for measuring the concentration of biological particles in a flow of medium, comprising at least one test cell having a vibratory element disposed to contact medium flowing through the cell; drive means for vibrating said element and a position transducer for providing an output determined by the position of the element; conduit means for directing medium from said flow to the test cell; means for separating biological particles from the medium and control means for receiving said transducer output and calculating a density value therefrom, the control means being arranged to calculate separate density values for medium containing biological particles and medium from which biological particles have been separated and to provide therefrom a measure of the concentration of biological particles.

Advantageously, the control means includes drive circuitry which amplifies said transducer output, said amplified signal being presented as an input to the vibratory element drive means, whereby the vibratory element is in use brought to a resonant frequency indicative of density.

Suitably, said conduit means includes a bypass flow path upstream of the test cell, the separating means being located in said bypass, thereby provided valve means operable by said control means selectively to divert flow through said bypass.

Alternatively, the apparatus comprises two said test cells connected in parallel flow paths, the separating means being provided in one parallel flow path upstream of the associated test cell.

Preferably, the vibratory element is shaped as a conduit through which the medium passes.

In one form of the invention said conduit is formed of piezoelectric material and wherein said drive means acts to supply an exciting voltage to the piezoelectric material.

In another aspect the present invention consists in a method of measuring the concentration of biological particles suspended in a fluid medium, wherein two density measurements are made each comprising the excitation of a vibratory element in contact with the medium and the determination of a density value from the vibratory motion of the element, the measurements being separated by a change in a parameter having a known differential effect on the respective contribution to density of the biological particles and the medium, whereby a comparison of the two measured values is indicative of the concentration of the biological particles.

Preferably said parameter is the temperature of the suspension.

Alternatively said parameter comprises the natural frequency of the vibratory element.

It will be appreciated that this invention provides a method of determining the amount of biological material—typically the concentration of bacteria—which is rapid and operationally straightforward. The method is therefore ideally suited to on-line use in monitoring fermentation processes and the like. It has been established that the measurement of density is a reliable indicator of the number of bacteria or other microorganisms per unit volume and, since the measured parameter is in the preferred form the resonant frequency of a vibratory element, the highly accurate techniques that are available for the measurement of frequency will ensure good sensitivity.

In certain cases, it will be convenient to practice this invention with a probe capable of insertion into an existing chamber or pipeline. The portion of the chamber or pipeline immediately surrounding the inserted probe can then be regarded as forming part of the test cell.

It is an object of a further form of this invention to provide improved apparatus in the form of a probe for use in measuring the amount of biological material in a fluid medium.

Accordingly, the present invention further consists in probe means for use in measuring the amount of biological material in a fluid medium comprising first and second vibratory elements mounted so as in use to contact the medium; means for exciting the elements such that the vibrational movement thereof is indicative of density; shield means surrounding one element and impervious to biological material so the effect on the movement of that element is due to the medium along and means for comparing the movements of the two elements to derive a measure of the amount of biological material.

Preferably each vibratory element is formed of piezoelectric material.

The invention will now be described by way of example with reference to the accompanying drawings in which.

Figure 1:
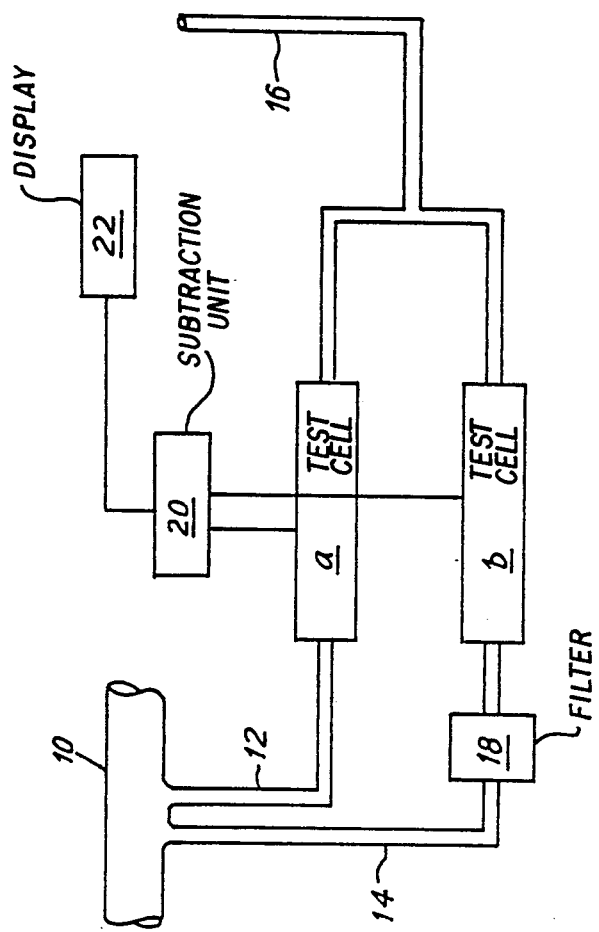
FIG. 1 is a diagram showing apparatus according to this invention.
Figure 2:
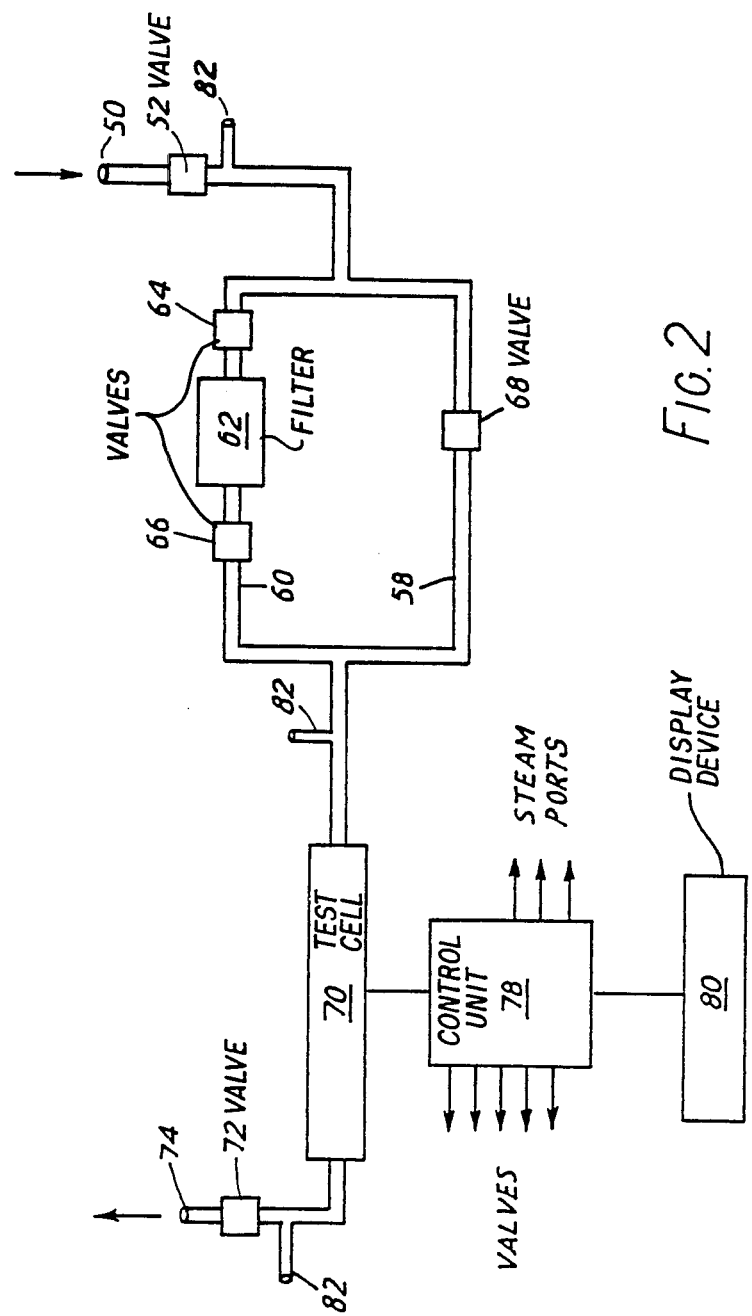
FIG. 2 is a diagram showing a further embodiment of this invention.
Figure 3:
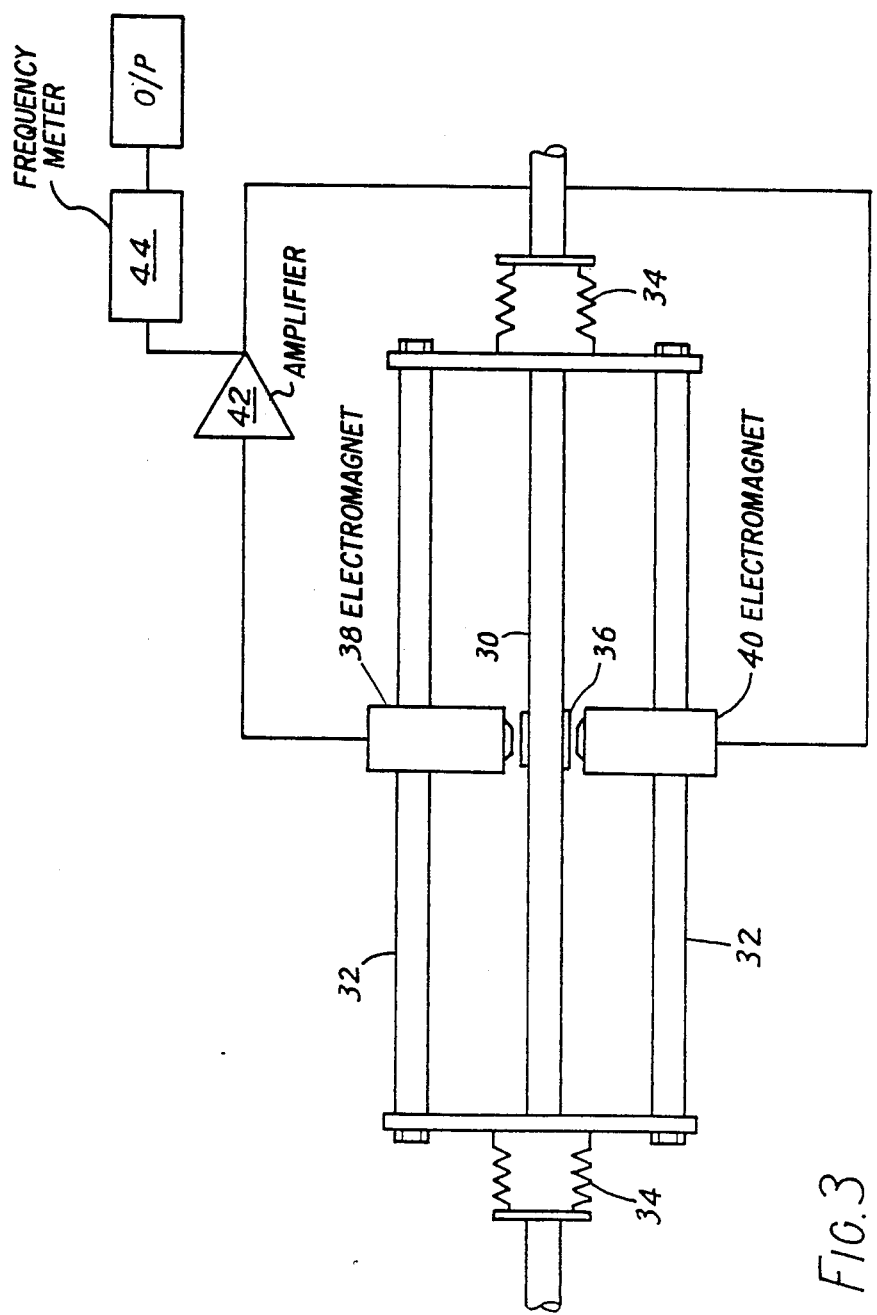
Figure 4:
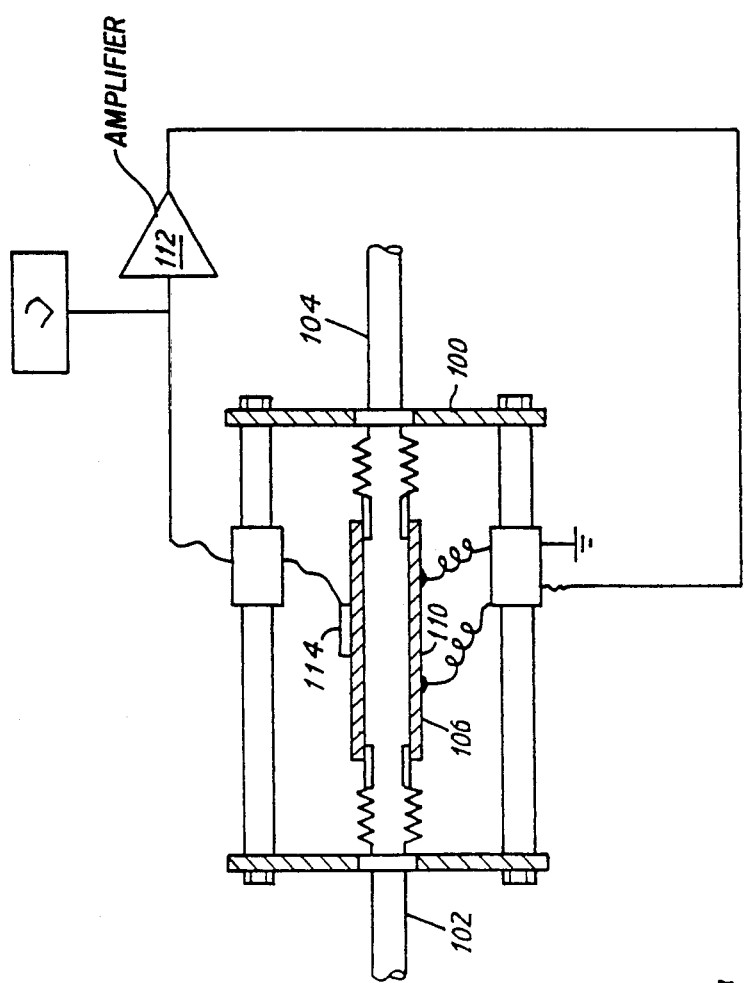
Figure 5:
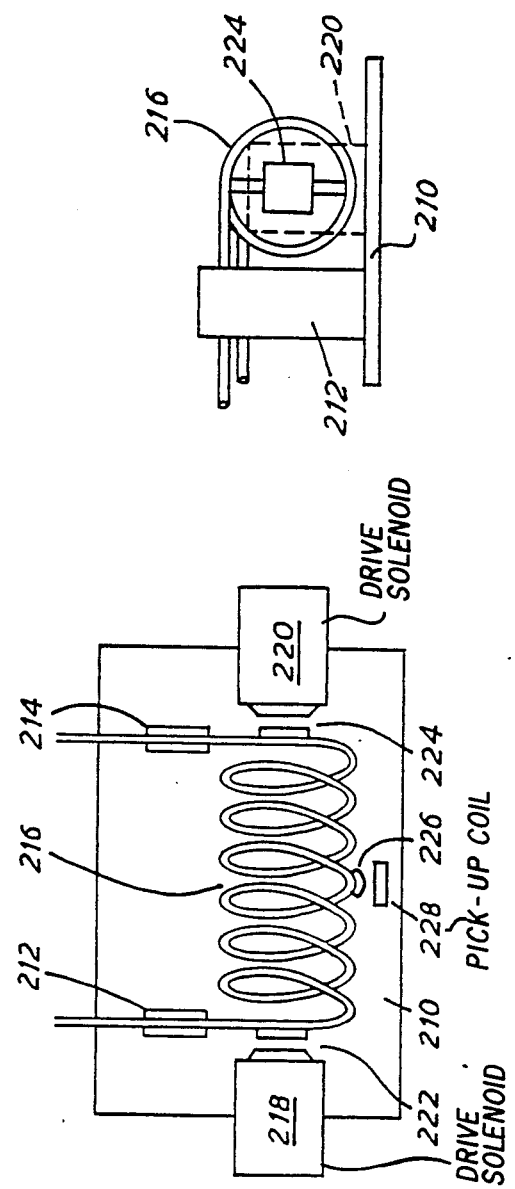
Figure 6:
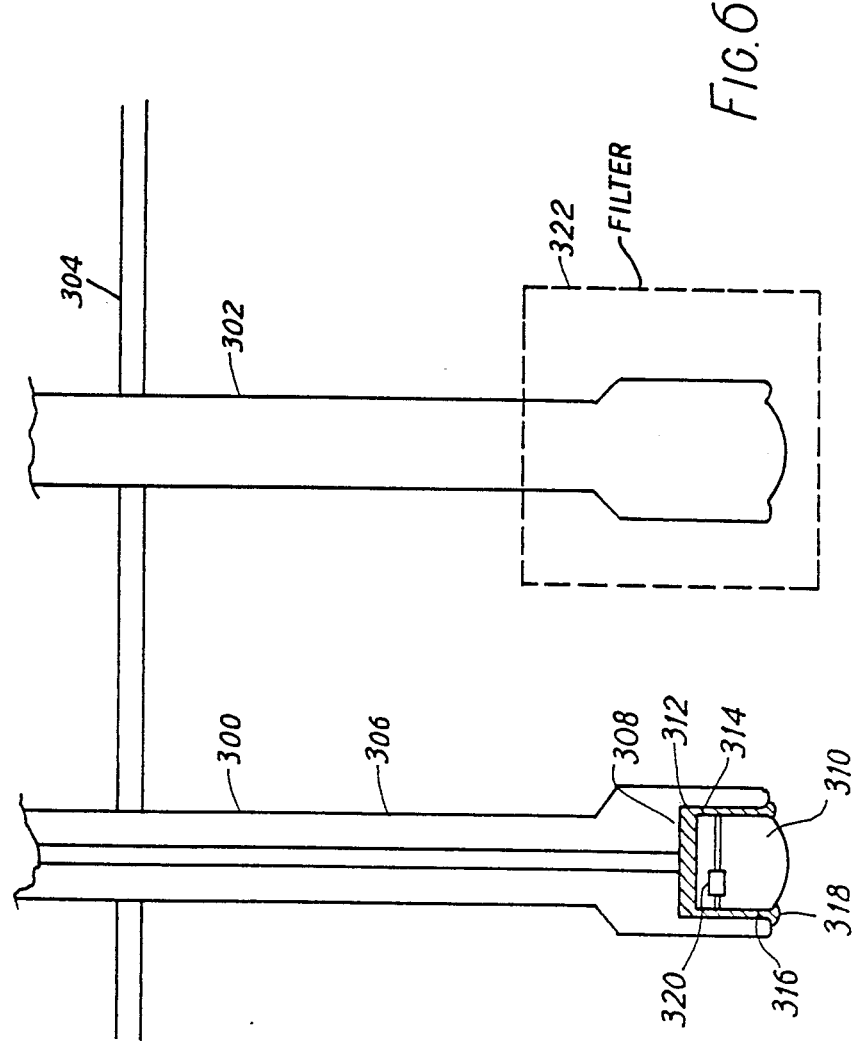
Figure 7:
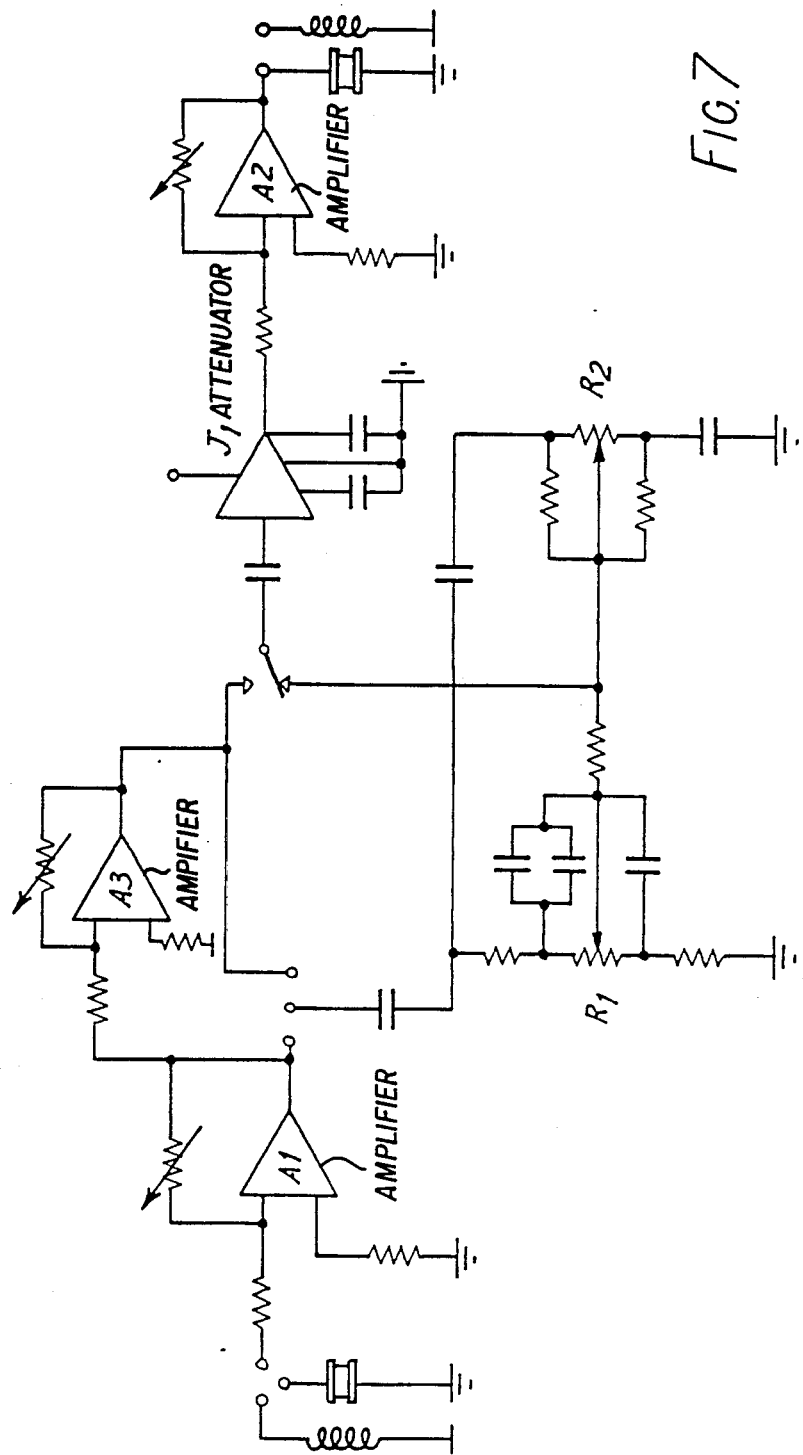
Figure 8:
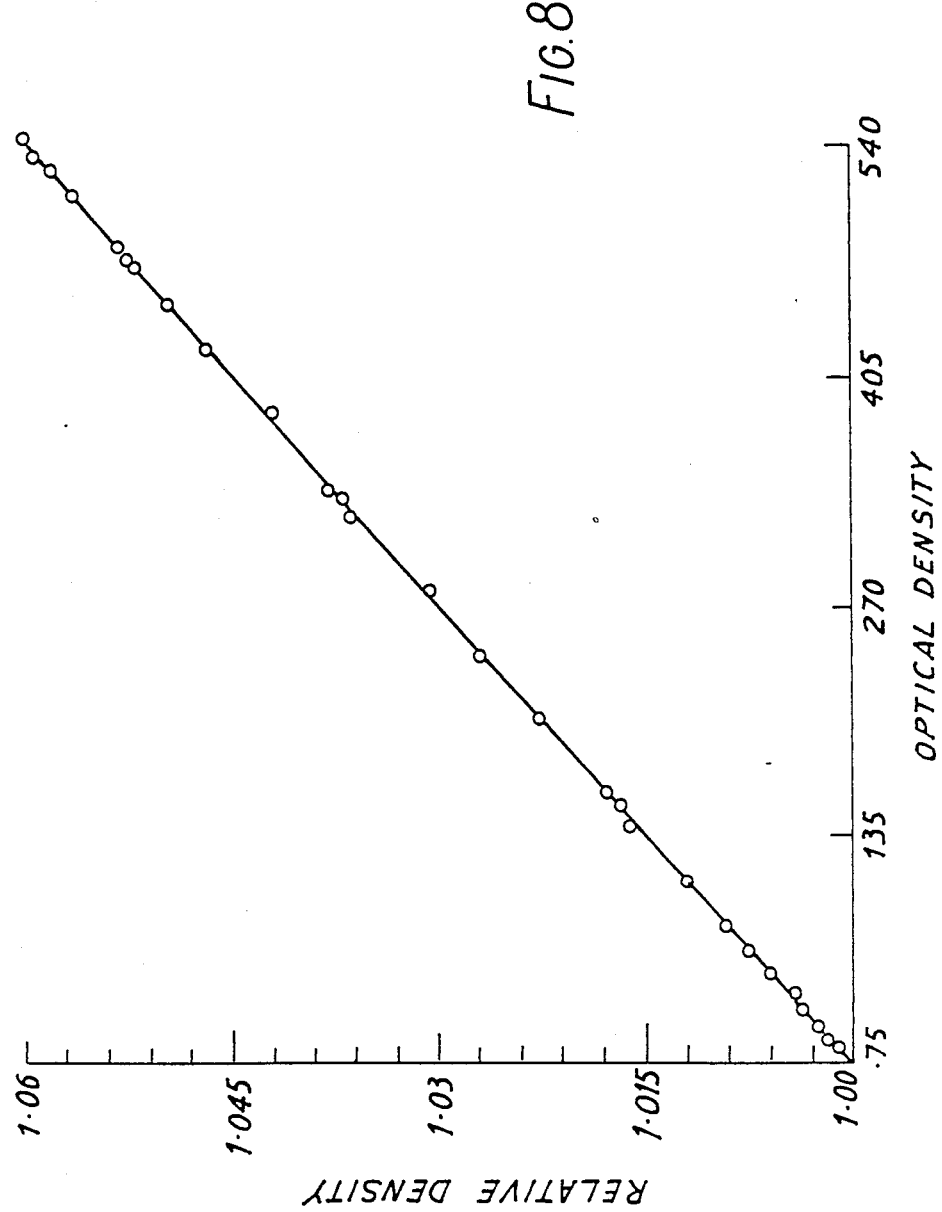

FIG. 3 illustrates one form of test cell to be used in the apparatus of FIG. 1 or FIG. 2, FIG. 4 illustrates an alternative test cell, FIGS. 5a and 5b illustrate a further, alternative test cell, FIG. 6 illustrates a further embodiment of the invention, FIG. 7 is a circuit diagram of an amplifier for use in the apparatus of FIG. 1 or FIG. 2, and FIG. 8 is a plot showing experimental results achieved in use of the invention.

Referring to FIG. 1, the pipeline shown at 10 forms part of a biological reactor, it being necessary to monitor continuously the number of bacteria per unit volume in the nutrient medium flowing along the pipeline. Parallel flow paths 12 and 14 branch from the pipeline 10 and are reconnected in conduit 16 which may return to the pipeline 10 or be taken to waste, whichever is preferred.

There is provided in each parallel flow path a test cell which will be described in detail hereinafter. The two test cells, designated a and b, provide respective output signals which are indicative of the density of the medium flowing through the test cell at that time. Parallel flow path 14 contains, in addition to the test cell b, a filter 18 having a pore size selected to separate bacteria from the flowing medium.

The two test cell outputs are taken to a subtraction unit 20 providing an output to a display 22 which is calibrated in numbers of bacteria per unit volume.

Referring now to FIG. 3, one example of a test cell will be described. Flow through the test cell passes along a stainless steel tube 30 which is supported at each end in a rigid frame 32 by means of respective PTFE bellows 34. The stainless steel tube carries at its midpoint a pair of opposed ferro-magnetic studs 36. In alignment with these studs, there are carried on the frame 32 a pair of polarised electro-magnets 38 and 40.

On transverse vibration of the tube 30, a voltage induced in electro-magnet 38 is amplified by amplifier 42 and a current supplied to electro-magnet 40. The amplifier is selected to have a gain exceeding the system attenuation and to have a very flat phase response. The tube is therefore driven to a resonant frequency determined by the fixed parameters of the apparatus and by the mass contained within the tube.

The output of the amplifier is taken additionally to a frequency meter 44 providing a digital test cell output which is indicative of density.

Measurements of *E. coli* concentration made in this way have been compared with measurements using conventional optical density techniques. FIG. 8 is a multiple data set plot showing the excellent experimental agreement that has been obtained.

A second embodiment of this invention is illustrated in FIG. 2. An input port 50 arranged to receive flowing medium is connected via valve 52 with a through flow path 58 and a by-pass flow path 60 connected in parallel. The by-pass 60 includes a filter 62 with upstream and downstream valves 64 and 66. The filter 62 is preferably of the cross-flow dialysis type to avoid problems by fouling. Alternatively, a through flow filter can be employed with an ultrasonic or other on-line cleaning system. The flow path 58 is provided with a valve 68.

The two flow paths 58 and 60 combine to pass through a test cell 70 which may be as described in FIG. 3. Flow from the test cell passes through valve 72 to outlet port 74.

Control unit 78 operates the described valves so as to establish alternating flows, a first through the by-pass 60 and filter 62 to the test cell and a second through flow path 58 to the test cell. Density values produced by the test cell for the alternate flows are stored and a subtraction performed to derive a value for the density of biological matter. The number of bacterium per unit volume is derived from this and displayed on display device 80.

To enable effective sterilization of the described apparatus, steam inlet/outlet ports 82 are provided at three locations in the apparatus. These are under the control of the control unit 80 and enable the apparatus to be purged section by section with appropriate settings of the shut-off valves.

In an alternative method according to this invention, a test cell such as that shown in FIG. 3 is used without a filter or other device for separating biological particles from the medium. Instead, two density measurements are made each in the manner described above with the flowing suspension brought to two different temperatures. This may be achieved by the use of a water jacket or similar device for stabilising the temperature of the test cell or, alternatively, by conditioning the flowing suspension at the required temperature before passing it through the test cell.

It has been found that the rate of decrease of medium density exceeds that of the biological particles so that by comparing the total density measurements at two temperatures, a determination can be made of the concentration of biological particles.

Referring now to FIG. 7, a preferred form of amplifier is shown for use with the above described test cell. The requirements for this amplifier are that the gain and phase shift should be substantially constant for the frequencies of transverse mode resonance over the range of densities likely to be encountered but that the higher frequencies associated with longitudinal or bell mode resonance should be severely attenuated. It is usually not possible to predict the natural resident frequency of a test cell in each mode and in order to maximize the usable bandwidth of the amplifier without including higher modes of resonance, it is desirable to have an amplifier the frequency response of which can be tailored in use.

In the circuit diagram which is FIG. 7, A1 is a variable gain operational amplifier serving as a first stage buffer and impedence matching stage. A further amplification stage comprising operational amplifier A3 may be switched in or not depending on gain requirements but if no gain is required the gain is set to 1 to maintain phase relationships. The bandwidth of the amplifier is determined by a filter network including variable logarithmic resistors R1 and R2 which set the limits of the filter pass band. Stage J1 is a controlled attenuator which functions to limit the system gain. The final stage comprises a further operational amplifier of variable gain.

By the use of the described arrangement, an amplifier is provided which has a substantially linear response over a frequency range which can be tailored to cover the anticipated density range but to avoid unwanted resonance modes.

There is shown in FIG. 4 an alternative test cell according to this invention. A rigid frame 100 is connected to the inlet and outlet feed pipes 102 and 104. A cylinder 106 formed of lead zirconate titanate is aligned coaxially with the feed pipes and is coupled to the frame by means of PTFE bellows one at each end of the cylinder. In this way, sample flows from the inlet feed pipe through the cylinder to the outlet feed pipe.

Spaced electrodes 110 on the cylinder are electrically connected to one ground and the other to the output of an amplifier 112 which may be substantially as described in FIG. 6. A pickup 114, which may also be of lead zirconate titanate is mounted on the exterior of the cylinder and serves as a position transducer the output of which is connected to the input of the amplifier. It may be desirable to modify the amplifier shown in FIG. 6 by the addition of an impedance matching circuit at the output.

The manner of operation of this test cell is analogous with that previously described. The cylinder of piezoelectric material is fashioned as a thickness expander, that is to say it contracts and expands radially. The cylinder is excited to mechanical resonance through the described positive feedback path and the frequency of resonance is indicative of the density of the fluid contained within the cylinder. This test cell has the advantage, as compared with that shown in FIG. 3, that no separate drive coil is required. The piezoelectric cylinder serves both as the transducer and as the vessel defining the test volume. In a modification, it may be possible to omit the pickup and to use the piezoelectric cylinder, or parts of it, also as the position transducr. A further advantage of this embodiment of the invention is that between test runs, power may be applied to the piezoelectric cylinder to drive it into high amplitude vibration for cleaning purposes. This is advantageously combined with steam purging as described above and will result in a particularly effective decontamination procedure.

Referring to FIG. 5a and 5b, the apparatus comprises a rigid base plate 210 from which rise two mounting pillars 212 and 214. A coil 216 of thin stainless steel tubing is secured at opposite ends to the pillars 212, 214; the tube ends passing through the pillars to form fluid inlet and outlet ports. Between the two pillars, the coil has several turns which are freely suspended.

Drive solenoids 218 and 220 are disposed one at each end of the base 210. These solenoids cooperate respectively with ferromagnetic pole pieces 222 and 224 carried on opposite ends of the coil 216. At the coil midpoint, there is provided a small piezoelectric transducer 226 which cooperates with a fixed pick-up coil 228 to serve as a position/feedback transducer.

The pick-up coil 228 provides an input to amplifier (not shown), the output of which is connected in antiphase across the two drive solenoids 218 and 220. The amplifier is selected to have a gain which exceeds the losses of the electromechanical system and to have a broad bandwidth.

In operation, sample fluid is passed through the coil either continuously—if the rate at which the sample density changes is small compared with the fluid travel time through the coil—or alternatively in a step-wise manner. Inevitable background vibrations will result in slight movement of the coil which is detected in pick-up 228 with the effect that the movement is amplified through forces applied at opposite ends of the coils through the solenoids. In this way, the electromechanical system is brought to resonance at a frequency which is determined by the natural frequency of the coil and the mass of fluid contained therein. The resonant frequency is measured and passed to a display device (not shown) which may be calibrated in suitable density units.

The coil 216 has a length which greatly exceeds the tube thickness. In the described example, the length of the tube is 300 mm and the thickness ½ mm giving a length to thickness ratio of 600.

This test cell, which has particular advantages in use with the present invention, is described and claimed in Patent Application Ser. No. 832,713 filed on the same day by the same Applicants.

Referriing now to FIG. 6, a further embodiment of this invention is illustrated. In certain applications, it will be more convenient to insert a test probe in an existing chamber or feed line of a biological reactor than to divert flow to a test cell. In the Figure, two probes 300 and 302 are inserted through respective ports in a chamber wall 304. Internally, the two probes are identical and only probe 300 will be described. The probe comprises an elongated probe body 306 having an axial bore for accommodating electrical leads. The inner end of the probe body is enlarged and shaped to provide a housing 308 which opens at the free end of the probe. Positioned within this housing is a disc 310 of PZT material adapted to contract and expand axially. A rubber de-coupling cup 312 is positioned between the PZT disc and the housing and one face of the PZT disc is exposed to the sample. Electrical leads passing through the probe housing are connected with contact beads 314 and 316 positioned on opposite circular faces of the PZT disc. The annular gap between the end of the probe housing and the disc is closed by an epoxy seal 318. If necessary, a position transducer is located in cavity 320.

The manner of operation of the probe is essentially as described above in connection with the previous embodiments and the resonant freqency of the piezoelectric disc is indicative of the density of fluid in which the probe is inserted. Of course, the influence of the medium is "felt" at the surface of the disc rather than there being an isolated mass of medium which is caused to move with the vibration element.

The second probe 302 is surrounded by a filter 322 which is shown diagramatically in the drawing and which may take a variety of suitable forms. In a simple case, the filter comprises a cylinder of filter material having a pore size such that no biological particles can enter the region 324 immediately surrounding the probe free end. Sintered ceramics and glass are convenient filter materials. It can thus be seen that whilst probe 200 measures the total density of the fluid in the chamber defined by wall 204, probe 202 will measure the density of the medium only. The two probes are thus analogous with test cells a and b of the apparatus shown in FIG. 1 and their respective outputs are used as there described to provide a measure of the concentration of biological particles. If desired, the two probes may be combined in one structure.

This invention has been described by way of example only and numerous modifications are possible without departing from the scope of the invention. A variety of test cells and other apparatus have been described but it will be apparent to the skilled man that other structures can be used in which a vibratory element, in contact with the fluid whose density is to be measured, is brought to mechanical resonance at a frequency indicative of density. Forms of vibration densitometers developed—for example—in the petrochemical industry may be suitable for use in apparatus according to this invention although the particular test cells described in this specification are preferred for the reasons given.

In certain cases, the movement of the vibratory element may be monitored not by exciting the element to resonance and measuring the frequency but by applying an impulse to the element and noting the decay in vibratory movement. Alternatively, the time of propagation may be measured of a wave in the medium generated by the vibratory element. A second, receiving vibratory element may be provided or the first element may with suitable signed processing serve as both transmitter and receiver with waves in the medium reflected from the boundaries of the enclosure. These techniques provide information in a form requiring considerable further processing before revealing a measure of the concentration of microorganisms. For this reason, resonance techniques are usually preferred.

It has been described that under certain circumstances, two measurements of density can be made at different temperatures rather than on separated and non-separated sample flows. In yet another alternative, the parameter which is varied between measurements may be the natural frequency of the vibratory element rather than temperature.

With some biological systems, a single measurement of density will suffice provided that a previous calibration has confirmed that density is—in the relevant range—a single valued function of the concentration of bacteria or other biological particles. This measurement can be made, for example, with a probe as shown at 300 in FIG. 6. The probe, together with the surrounding portion of the chamber or pipeline into which it is inserted can then be regarded as a test cell.

This invention has been described primarily in relation to the determination of bacteria concentrations. As will be self evident the invention is applicable to the determination of concentrations of other microorganisms and indeed, generally to measuring amounts of biological material in fluid media.

We claim:

1. A method of determining the concentration of microorganisms suspended in a fluid medium comprising the steps of exciting to vibratory motion a vibratory element in contact with a sample of a suspension of said microorganisms in said fluid medium, monitoring said vibratory motion to obtain a value of the density of the suspension and deriving from said density value a measure of the concentration of said microorganisms.

2. A method according to claim 1, wherein said steps of exciting and monitoring the motion of a vibratory element are repeated after removal of said microorganisms so as to obtain a value of the density of the medium and wherein said measure of the concentration of microorganisms is derived from a comparison of density values for the suspension and for the medium.

3. A method according to claim 1 wherein the vibratory element is brought to resonance through feedback and the resonant frequency is measured to indicate density.

4. A method of measuring the concentration of biological cells in a flowing medium using at least one test chamber having a vibratory element the motion of which is monitored to provided a measure of the density of the flow in the test chamber, comprising the steps of directing the flow of medium containing the biological cells through the test chamber; obtaining a first measure of density; separating biological cells from the medium; directing the separated medium through the test chamber; obtaining a second measure of density and deriving from comparison of said first and second measures of density a value for the concentration of biological cells in the medium.

5. A method according to claim 4, wherein one test chamber is used and the step of directing medium from which biological cells have been removed through the test chamber comprises diverting the flow along the path containing a filter adapted to remove the biological cells.

6. A method according to claim 4, wherein two test chambers are used and the step of directing medium from which biological cells have been removed through one of the test chambers comprises splitting the flowing medium into two flow paths each containing a test chamber, one flow path including a filter upstream of the associated test chamber.

7. A method according to claim 4 wherein the vibratory element is brought to resonance through feedback and the resonant frequency is measured to indicate density.

8. Apparatus for measuring the concentration of biological cells in a flow of medium, comprising at least one test chamber having a vibratory element disposed to contact medium flowing through the chamber; drive means for vibrating said element and a position transducer for providing an output determined by the position of the element; conduit means for directing medium from said flow to the test chamber; means for separating biological cells from the medium and electrical circuit means including calculating means for receiving said transducer output and calculating a density value therefrom, the calculating means being arranged to calculate separate density values for medium containing biological cells and medium from which biological cells have been separated and to provide therefrom a measure of the concentration of biological cells.

9. Apparatus according to claim 8, wherein the electrical circuit means includes drive circuitry which amplifies said transducer output, said amplified signal being presented as an input to the vibratory element drive means, whereby the vibratory element is in use brought to a resonant frequency indicative of density.

10. Apparatus according to claim 8, wherein said conduit means includes a bypass flow path upstream of the test chamber, the separating means being located in said bypass, thereby providing valve means operable by said electrical circuit means selectively to divert flow through said bypass.

11. Apparatus according to claim 8, wherein the aparatus comprises two said test chambers connected in parallel flow paths, the separating means being provided in one parallel flow path upstream of the associated test chamber.

12. Apparatus according to claim 8, wherein the vibratory element is shaped as a conduit through which the medium passes.

13. A method of measuring the concentration of microorganisms suspended in a fluid medium, wherein two density measurements are made each comprising the excitation to vibratory motion of a vibratory element in contact with a sample of a suspension of said microorganisms in said fluid medium and the determination of a density value of the suspension from the vibratory motion of the element, the measurements being made at different temperatures of said suspension and a comparison of the two measured values is made to provide an indication of the concentration of the microorganisms.

14. A method of monitoring the concentration of biological cells suspended in a fluid medium, the density of which medium varies with variation in said concentration, comprising the repeated performance of a seried of steps, said series of steps comprising the steps of exciting into vibratory motion a vibratory element in contact with a sample of the suspension of said biological cells in said fluid medium; monitoring said vibratory motion to obtain a value for the suspension density; preparing a sample of said fluid medium by removing from said suspension said biological cells; exciting into vibratory motion a vibratory element in contact with said sample of said fluid medium; monitoring said vibratory motion to obtain a value for the medium density and comparing the values of suspension density and medium density to obtain a measure of the concentration of biological cells.

* * * * *